(12) United States Patent
Fredenberg et al.

(10) Patent No.: US 10,881,358 B2
(45) Date of Patent: Jan. 5, 2021

(54) TOMOSYNTHESIS APPARATUS AND METHOD FOR CHARACTERIZING A LESION IN A BREAST

(71) Applicant: KONINKLIJKE PHILIPS N.V., Eindhoven (NL)

(72) Inventors: Jon Erik Fredenberg, Vallentuna (SE); Klaus Erhard, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 147 days.

(21) Appl. No.: 15/760,643

(22) PCT Filed: Sep. 28, 2016

(86) PCT No.: PCT/EP2016/073027
§ 371 (c)(1),
(2) Date: Mar. 16, 2018

(87) PCT Pub. No.: WO2017/060133
PCT Pub. Date: Apr. 13, 2017

(65) Prior Publication Data
US 2018/0256117 A1   Sep. 13, 2018

(30) Foreign Application Priority Data
Oct. 5, 2015 (EP) .................................. 15188345

(51) Int. Cl.
*A61B 6/02*      (2006.01)
*A61B 6/00*      (2006.01)

(52) U.S. Cl.
CPC .............. *A61B 6/025* (2013.01); *A61B 6/469* (2013.01); *A61B 6/482* (2013.01); *A61B 6/502* (2013.01); *A61B 6/4241* (2013.01)

(58) Field of Classification Search
CPC ......... A61B 6/025; A61B 6/469; A61B 6/482; A61B 6/502; A61B 6/4241
(Continued)

(56) References Cited

U.S. PATENT DOCUMENTS 5,657,362 A * 8/1997 Giger .................... G06T 7/0012
378/37
6,173,034 B1 * 1/2001 Chao ...................... A61B 6/482
378/37
(Continued)

FOREIGN PATENT DOCUMENTS

WO   2013035026   3/2013
WO   2014/097026   6/2014
(Continued)

OTHER PUBLICATIONS

Fredenberg, et al., "Measurement of breast-tissue x-ray attenuation by spectral mammography: solid lesions", Phys Med Biol (submitted for publication, 2015, published 2016.
(Continued)

*Primary Examiner* — Blake C Riddick
(74) *Attorney, Agent, or Firm* — Larry Liberchuk

(57) ABSTRACT

The present invention relates to an apparatus for characterization of a feature in a body part. It is describe to provide (210) tomosynthesis medical data comprising a plurality of images of the body part, wherein the plurality of images comprise image data associated with a plurality of rays of radiation that have passed through the body part, wherein the image data comprises spectral data associated with at least two photon energy levels of the plurality of rays of radiation, wherein the medical data comprises data of the feature. A delineated boundary of the feature is determined (220). At least one material composition of the body part inside the delineated boundary is determined (240) comprising a function of the spectral data inside the delineated boundary. The
(Continued)

feature is characterised (250) as a function of the at least one material composition inside the delineated boundary of the feature. Data representative of the feature is output (260).

9 Claims, 6 Drawing Sheets

(58) Field of Classification Search
USPC .................................. 378/2, 4, 5, 37, 53, 62
See application file for complete search history.

(56) References Cited

U.S. PATENT DOCUMENTS

| | | | | |
|---|---|---|---|---|
| 2004/0202279 | A1* | 10/2004 | Besson | A61B 6/06 378/37 |
| 2004/0253652 | A1* | 12/2004 | Davies | A61B 5/04082 435/7.23 |
| 2006/0094950 | A1* | 5/2006 | Ning | A61B 6/032 600/407 |
| 2006/0167355 | A1* | 7/2006 | Rico | A61B 6/502 600/407 |
| 2006/0177125 | A1* | 8/2006 | Chan | G06K 9/00 382/154 |
| 2006/0269040 | A1 | 11/2006 | Mertelmeier | |
| 2007/0019784 | A1 | 1/2007 | Ting | |
| 2009/0208085 | A1 | 8/2009 | Muller | |
| 2010/0046814 | A1* | 2/2010 | Dewaele | G06T 7/0012 382/128 |
| 2010/0266179 | A1* | 10/2010 | Ramsay | G06T 7/0012 382/131 |
| 2012/0257808 | A1* | 10/2012 | Spitzer | G06T 5/008 382/131 |
| 2013/0136331 | A1 | 5/2013 | Hoernig | |
| 2013/0144167 | A1* | 6/2013 | Lee | A61B 8/085 600/443 |
| 2014/0140604 | A1* | 5/2014 | Carton | A61B 6/481 382/132 |
| 2016/0213344 | A1* | 7/2016 | Yi | A61B 6/5282 |
| 2016/0242733 | A1* | 8/2016 | Lenox | A61B 8/0825 |

FOREIGN PATENT DOCUMENTS

| | | |
|---|---|---|
| WO | 2015/061582 | 4/2015 |
| WO | 2015/118033 | 8/2015 |

OTHER PUBLICATIONS

Wang, et al., "Non-invasive classification of microcalcifications with phase-contrast X-ray mammography" Nature communications 5 (2014).

Erhard, et al., "Characterization of Cystic Lesions by Spectral Mammography: Results of a Clinical Pilot Study", Investigative Radiology, 2016.

* cited by examiner

TOMOSYNTHESIS APPARATUS AND METHOD FOR CHARACTERIZING A LESION IN A BREAST

CROSS REFERENCE TO RELATED APPLICATIONS

This application is the U.S. National Phase application under 35 U.S.C. § 371 of International Application No. PCT/EP2016/073027, filed Sep. 28, 2016, published as WO 2017/060133 on Apr. 13, 2017, which claims the benefit of European Patent Application Number 15188345.1 filed Oct. 5, 2015. These applications are hereby incorporated by reference herein.

FIELD OF THE INVENTION

The present invention relates to an apparatus for characterization of a feature in a body part, to a medical system for characterization of a feature in a body part, and to a method for characterization of a feature in a body part, as well as to a computer program element and a computer readable medium.

BACKGROUND OF THE INVENTION

Spectral X-ray imaging, i.e. photon energy resolved X-ray imaging, has been applied in mammography. For example, WO2014/097026A1 describes utilizing spectral image data with respect to measuring breast thickness in mammography. It has also previously been shown that the discrimination of (likely benign) cystic from (potentially malignant) solid lesions is feasible from a spectral mammogram, which has the potential to improve the specificity in mammography screening. In general, spectral X-ray imaging allows differentiation between given tissue types, provided their spectral absorption characteristics differ measurably. However, the performance of using a spectral mammogram for the differentiation is hampered by having to make assumptions about the body part under examination, as well as overlap in the spectral information of the lesion types, for instance due to biological variation. For the application of discriminating between cystic and solid lesions, this means that a significant portion of solid lesions cannot be differentiated from cyst fluid. Spectral discrimination between malignant and benign micro-calcifications is even more challenging because of an almost complete overlap in the spectral information.

US 2007/019784A1 discloses an apparatus for characterisation of a feature in a body part with in particular an input unit configured to provide a processing unit with tomosynthesis medical data comprising spectral data associated with two photon energy levels.

WO 2015/061582 A2 discloses an apparatus for tomosynthesis using two photon energy levels wherein the processing unit is configured to determine a delineated boundary of a feature.

SUMMARY OF THE INVENTION

In order to mitigate the challenges of current implementations of tissue characterization, it would be advantageous to have an improved technique for characterization of a features in body parts.

The object of the present invention is solved with the subject matter of the independent claims, wherein further embodiments are incorporated in the dependent claims. It should be noted that the following described aspects of the invention apply also for the apparatus for characterization of a feature in a body part, the medical system for characterization of a feature in a body part, the method for characterization of a feature in a body part, and for the computer program element and the computer readable medium.

According to a first aspect, there is provided an apparatus for characterization of a feature in a body part, comprising:
an input unit;
a processing unit; and
an output unit.

The input unit is configured to provide the processing unit with tomosynthesis medical data comprising a plurality of images of the body part, wherein the plurality of images comprise image data associated with a plurality of rays of radiation that have passed through the body part, wherein the image data comprises spectral data associated with at least two photon energy levels of the plurality of rays of radiation, wherein the medical data comprises data of the feature. The processing unit is configured to determine a delineated boundary of the feature. The processing unit is also configured to determine at least one material composition of the body part inside the delineated boundary comprising a function of the spectral data inside the delineated boundary. The processing unit is also configured to characterise the feature as a function of the at least one material composition inside the delineated boundary of the feature. The output unit is configured to output data representative of the feature. The processing unit is configured to determine at least one material composition of the body part inside at least one portion of at least one image of the plurality of images as a function of the spectral data inside at least a part of the at least one portion, wherein the at least one portion is outside the delineated boundary. The processing unit is configured to determine at least one material composition of the body part inside the delineated boundary dependent on the at least one material composition inside the at least one portion that is outside the delineated boundary.

In the discussion that follows, the medical data can be considered to be a volume stack of X-ray images.

In an example, the medical data are a plurality of images relating to a plurality of depths within the body part, for example a plurality of 2D X-ray images relating to a plurality of depths within the body part.

In an example, the plurality of images are in effect slices that are substantially parallel to each other, oriented normal to the viewer, at different depths through the body part. In other words, when the plurality of images is placed into a stack the plurality of images provides a 3D representation of the body part.

In an example, the apparatus can be used in tomosynthesis imaging or image display. In an example, the apparatus can be used in breast tomosynthesis imaging or image display. In this manner, in an example the apparatus can be applied to X-ray tomosynthesis.

In the following discussion, the words "lesion" and "feature" will be used interchangeably. Although the word lesion is commonly used for an abnormal feature, it is understood that what is discussed here in terms of lesions is applicable to any tissue features, normal or abnormal.

In this manner, it is possible to characterise a feature (for instance a lesion) in a tissue sample where the top and the bottom of the lesion are cleared from all other tissue types. In that case it is known a priori that rays passing through the lesion will only pass through the lesion and not pass any other tissue. The depth information provided from tomosynthesis data can then be used in combination with the spectral data in the lesion region to characterise the lesion in cases where the spectral data overlap, for instance because of natural variation of the tissue. Such lesion characterization in tissue samples may find application for instance in the field of pathology.

By using the spectral information (X-ray data obtained at, at least, two photon energy levels), the material composition outside of a delineated (or annotated or demarked) feature can be determined, and the material composition inside the delineated feature can be determined by removing the influence of the body part outside of the delineated feature. In an example, the processing unit is configured to determine the at least one material composition of the body part inside the at least one first region comprises interpolation of the at least one material composition in the at least one second region into the at least one first region.

In an example, the at least one portion that is outside the delineated boundary comprises at least one first region and at least one second region, wherein the at least one first region is defined such that every ray of the plurality of rays that passes through the at least one first region also passes through the feature as defined by the delineated boundary and wherein every ray of the plurality of rays that have not passed through the feature as defined by the delineated boundary also have not passed through the at least one first region, and wherein the processing unit is configured to determine at least one material composition of the body part inside the at least one second region as a function of the spectral data in the at least one second region and the processing unit is configured to determine the at least one material composition of the body part inside the at least one first region as a function of the at least one material composition in the at least one second region.

In other words, by using the depth information available from the tomosynthesis data along with the spectral information, the material composition outside of a delineated feature can be determined with higher precision than would be possible without the depth information, and the material composition inside the delineated feature can accordingly be determined with higher precision by a more precise removal of the influence of the body part outside of the delineated feature.

To summarize what has been discussed so far, the additional spatial information available in tomosynthesis is used together with the spectral information available from having more than one X-ray energy level to characterise features or to differentiate between different feature types. This scheme enables differentiation between features with overlapping spectral data, and relaxes the need for additional assumptions when characterizing features embedded in other tissue.

In an example, the at least one portion outside the delineated boundary is in a specific image of the plurality of images and wherein the processing unit is configured to determine the at least one material composition of the body part inside the at least one first region as a function of the at least one material composition in the at least one second region for the specific image.

In an example, the processing unit is configured to determine a geometrical distance travelled by at least one ray of the plurality of rays through the body part, and/or the processing unit is configured to determine a geometrical distance travelled by at least one ray of the plurality of rays through the feature.

In this manner, the processing unit is able to differentiate between features that have the same effective atomic number but that have different densities.

In an example, the feature is annotated directly in at least one of the plurality of images and wherein the processing unit is configured to determine the delineated boundary of the feature as a function of the annotated feature.

In an example, the medical data comprises a combined image of at least two of the plurality of images and wherein the feature is annotated directly in the combined image, and wherein the processing unit is configured to back propagate the annotated feature in the combined image into at least one of the plurality of images that comprises data of the feature to determine the delineated boundary of the feature.

In other words, a delineated (or annotated or demarked) boundary of the feature, can either be in a 2D representation (combined image) of the 3D reconstruction or in one or more slices out of a stack of slice reconstructions, i.e., at least one image of the plurality of images. Furthermore, the delineated boundary of the feature may only describe a part of the feature's boundary. For example the delineated boundary might be the contour of the feature in one or more slices or in a 2D combined image, but may not contain information of the boundary of the feature in an orthogonal direction (depth direction orthogonal to the reconstructed slices).

In an example, the delineated boundary of the feature comprises a three-dimensional shape model of the feature, and wherein the processing unit being configured to determine the at least one material composition of the body part inside the delineated boundary comprises utilising the three-dimensional shape model of the feature.

In this manner, the spatial extent of the feature can be employed for characterization of the feature, even if the spatial information from the tomosynthesis data and/or from the lesion annotation is limited.

In an example, the processing unit being configured to determine the at least one material composition of the body part inside the delineated boundary comprises utilising calculated spectral features of at least two materials for the at least two energies of the plurality of rays of radiation.

In this manner, calibration data from two or more reference materials can be used for characterization of the feature by the processing unit. The energy-dependent attenuation of any material can, in general, be described by a combination of two or more other materials.

According to a second aspect, there is provided a medical system for characterization of a feature in a body part, the system comprising:

an image acquisition unit;

an apparatus for characterization of a feature in a body part according to any of the preceding examples; and a display unit. The image acquisition unit is configured to provide the medical data of a body part. The display unit is configured to display at least one of the plurality of X-ray images along with data representative of the feature.

According to a third aspect, there is provided a method for characterization of a feature in a body part, comprising:

a) providing tomosynthesis medical data comprising a plurality of images of the body part, wherein the plurality of images comprise image data associated with a plurality of rays of radiation that have passed through the body part, wherein the image data comprises spectral data associated with at least two energies of the plurality of rays of radiation, wherein the medical data comprises data of the feature;

b) determining a delineated boundary of the feature;

c) determining at least one material composition of the body part inside at least one portion of at least one image of the plurality of images as a function of the spectral data inside at least a part of the at least one portion, wherein the at least one portion is outside the delineated boundary; and wherein step d) comprises determining at least one material composition of the body part inside the delineated boundary dependent on the at least one material composition inside the at least one portion that is outside the delineated boundary;
d) determining at least one material composition of the body part inside the delineated boundary comprising a function of the spectral data inside the delineated boundary;
e) characterizing the feature as a function of the at least one material composition inside the delineated boundary of the feature; and
f) outputting data representative of the feature.

In an example, the at least one portion that is outside the delineated boundary comprises at least one first region and at least one second region, wherein the at least one first region is defined such that every ray of the plurality of rays that passes through the at least one first region also passes through the feature as defined by the delineated boundary and wherein every ray of the plurality of rays that have not passed through the feature as defined by the delineated boundary also have not passed through the at least one first region, and wherein step c) comprises determining at least one material composition of the body part inside the at least one second region as a function of the spectral data in the at least one second region, and wherein step c) comprises determining the at least one material composition of the body part inside the at least one first region as a function of the at least one material composition in the at least one second region.

In an example, the at least one portion outside the delineated boundary is in a specific image of the plurality of images and wherein step c) comprises determining the at least one material composition of the body part inside the at least one first region as a function of the at least one material composition in the at least one second region for the specific image.

In an example, step c) comprises interpolating the at least one material composition in the at least one second region into the at least one first region.

In an example, the method comprises determining a geometrical distance travelled by at least one ray of the plurality of rays through the body part, and/or determining a geometrical distance travelled by at least one ray of the plurality of rays through the feature.

In an example, the method comprises annotating the feature directly in at least one of the plurality of images and determining the delineated boundary of the feature as a function of the annotated feature.

In an example, the medical data comprises a combined image of at least two of the plurality of images and wherein the method comprises annotation of the feature directly in the combined image, and wherein determining the delineated boundary of the feature comprises back propagating the annotated feature in the combined image into at least one of the plurality of images that comprises data of the feature by automatic retrieval of a focal plane.

In an example, the delineated boundary of the feature comprises a 3D shape model of the feature, and wherein determining the at least one material composition of the body part inside the delineated boundary comprises utilising the 3D shape model of the feature.

In an example, determining the at least one material composition of the body part inside the delineated boundary comprises utilising calculated spectral features of at least two materials for the at least two energies of the plurality of ray of radiation.

According to another aspect, there is provided a computer program element controlling apparatus as previously described which, in the computer program element is executed by processing unit, is adapted to perform the method steps as previously described. According to another aspect, there is provided a computer readable medium having stored computer element as previously described.

Advantageously, the benefits provided by any of the above aspects and examples equally apply to all of the other aspects and examples and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

X-ray tomosynthesis is a technique that creates three-dimensional (3D) image representations. For example, when applied to mammography, 3D image representations of the breast can be created. A 3D tomosynthesis image representation is typically created from a number of individual two-dimensional (2D) images, where the compilation of 2D images is referred to as a stack. An individual 2D image is referred to as a slice. Digital breast tomosynthesis enables 3D imaging of the breast and offers the potential of increased cancer detection rates and reduced recall rates from screening compared to standard 2D mammography.

Spectral imaging is a technique that utilizes the energy information of X-ray photons to extract material properties of an object, so-called material decomposition. When applied to mammography, spectral imaging can be used to extract the material composition of a breast.

Figure 1:
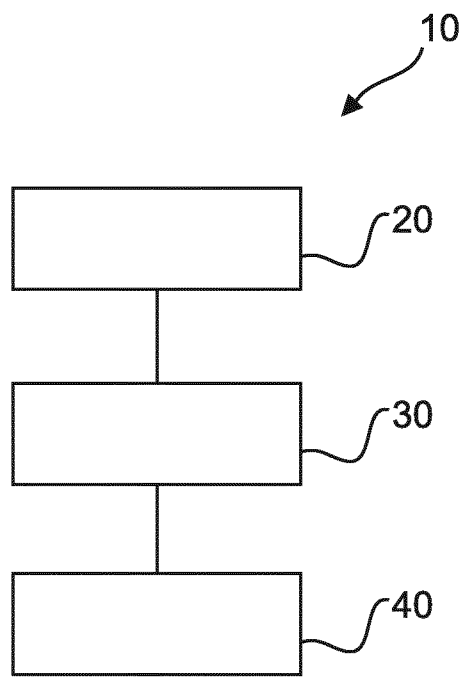
FIG. 1 shows an example of an apparatus for characterization of a feature in a body part.

FIG. 1 shows an apparatus 10 for characterization of a feature in a body part. The apparatus 10 comprises an input unit 20, a processing unit 30, and an output unit 40. The input unit 20 is configured to provide the processing unit 30 with tomosynthesis medical data comprising a plurality of images of the body part. The plurality of images comprise image data associated with a plurality of rays of radiation that have passed through the body part, wherein the image data comprises spectral data associated with at least two photon energy levels of the plurality of rays of radiation. The medical data comprises data of the feature. The processing unit 30 is configured to determine a delineated boundary 50, 70, 80 of the feature (see FIGS. 7 and 8 discussed below). The processing unit 30 is also configured to determine at least one material composition of the body part inside the delineated boundary 50, 70, 80 comprising a function of the spectral data inside the delineated boundary 50, 70, 80. The processing unit 30 is further configured to characterise the feature as a function of the at least one material composition inside the delineated boundary 50, 70, 80 of the feature. The output unit 40 is configured to output data representative of the feature.

In an example, the apparatus can be used in tomosynthesis imaging or image display. In an example, the apparatus can be used in breast tomosynthesis imaging or image display. In an example, the apparatus can be used in digital tomosynthesis imaging or image display.

In an example, the medical data is a volume stack of images, for example a stack of 2D images of a body reconstructed by a tomographic method such as tomosynthesis. In an example, each of the plurality of images is a single 2D image, for example where each of the plurality of images relates to a particular depth within the body part and the medical data (such as a volume stack) relates to a series of images at different depths through the body part.

In an example, the feature is a well-defined sub-volume within the body part under investigation.

A delineated (or annotated or demarked) boundary of the feature can either be in a 2D representation (combined image) of the 3D reconstruction, or in one or more slices out of a stack of slice reconstructions, i.e., at least one image of the plurality of images. Furthermore, the delineated boundary of the feature may only describe a part of the feature's boundary. For example the delineated boundary might be the contour of the feature in one or more slices or in a 2D combined image, but may not contain information of the boundary of the feature in an orthogonal direction (depth direction orthogonal to the reconstructed slices). The delineated boundary may also comprise a 3D shape model of the feature, so that the spatial extent of the feature can be employed for characterization of the feature, even if the spatial information from the tomosynthesis data and/or from the feature annotation is limited.

Additionally, a delineated boundary may be manually or automatically determined. Furthermore, in an example a computer-aided detection (CAD) related tool, or image processing algorithm, is used or applied to the plurality of images to automatically detect feature boundaries based on image analysis, and output only the result for the most relevant features. In this case the generation of feature boundaries would be part of the algorithm. In this manner the processing unit can automatically determine the delineated boundary of the feature in the plurality of images, where some of the plurality of images may not have a delineated boundary of the feature.

In an example, the output unit is configured to output an indication that the feature is benign or malignant. In an example, the output unit is configured to output an indication that the feature is a cystic lesion. In an example, the output unit is configured to output an indication that the feature is a solid lesion. In an example, the output unit is configured to output an indication that the feature is a likely benign calcification. In an example, the output unit is configured to output an indication that the feature is a likely malignant calcification. In an example, the output unit is configured to output the plurality of X-ray images. In an example, the output unit is configured to output at least one of the plurality of X-ray images. In an example, the output unit is configured to output a 2D representation of the 3D reconstruction comprising a combined image of the plurality of X-ray images. In an example, the output unit is configured to output imagery of the delineated boundary of the feature. In an example, the output unit is configured to output imagery of the delineated boundary of the feature annotated with the characterization of the feature.

In an example, the at least one material composition comprises a breast tissue composition. In an example, the at least one material composition is derived from spectral (photon energy) information. In an example, the at least one material composition comprises a cystic volume fraction. In an example, the at least one material composition comprises an equivalent cystic lesion diameter. In other words, in an example the material composition can be the division of the breast into some given materials such as adipose and glandular tissue. From this material composition, derived from a spectral material decomposition, various properties can be derived. These derived properties may comprise a cystic volume fraction, an equivalent cystic diameter, breast density value and the like.

In an example, spectral data are provided through the use of an energy-resolving photon counting detector.

According to an example, the processing unit is configured to determine at least one material composition of the body part inside at least one portion of at least one image of the plurality of images as a function of the spectral data inside at least a part of the at least one portion, wherein the at least one portion is outside the delineated boundary; and wherein, the processing unit is configured to determine at least one material composition of the body part inside the delineated boundary dependent on the at least one material composition inside the at least one portion that is outside the delineated boundary.

With respect to the processing unit being configured to determine at least one material composition of the body part inside at least one portion of at least one image of the plurality of images, in an example the following applies: A material composition in the reference region (outside the boundary, i.e. the lesion-free region) is computed from the spectral data in the reference region. No additional information is needed if it is assumed that this region is a combination of only two basis materials (adipose and glandular tissue for the example of a breast). This example involves solving a system of 2 equations (2 measured photon energy levels) and two unknowns (adipose and glandular tissue length per X-ray).

With respect to the processing unit being configured to determine at least one material composition of the body part inside the delineated boundary, in an example the following applies: A material composition inside the boundary (lesion region) is computed from the spectral data inside this region and dependent on the material composition outside the boundary (in the lesion-free region). This dependency is due to the interpolation of the surrounding tissue composition from the lesion-free region into the area of the lesion region to approximately solve a system of 2 equations (2 measured energies inside the lesion region) for four unknowns (adipose, glandular, cyst and solid tissue length per X-ray for the example of a breast). Substituting the unknown tissue lengths of adipose and glandular tissue inside the lesion region with the interpolated values from the lesion-free reference region makes it possible to solve this equation.

In this manner, the material composition within the delineated boundary can be determined and the dependency on the material composition outside the boundary is minimized.

In an example, characterizing the feature comprises determining the lesion type from a pre-defined selection. In an example, characterizing the feature comprises a calibrated spectral reconstruction. In an example, characterizing the feature comprises a calibrated spectral reconstruction based on spectral data acquired for various combinations of two basis materials. In other words, characterizing the feature comprises determining a system response to various combinations of two basis materials. In an example, the two basis materials are Aluminium (Al) and polyethylene (PE). In an example, the response is used to generate a look up table.

In an example, the feature, such as a suspected lesion or anomaly, is manually annotated by a radiologist and the processing unit determines the delineated boundary of the feature. In an example, the feature is automatically delineated through the use of image processing algorithms. In other words, a feature (such as a lesion) can be delineated or annotated in the tomosynthesis volume or in a 2D representation of the plurality of tomosynthesis slices to automatically derive a determined (or estimated) lesion region in the tomosynthesis volume reconstruction.

In an example, the spatial information available from the tomosynthesis data is used to determine the spatial extent of a feature (such as a lesion). In other words, the tomosynthesis data can be used to determine the distance through different constituent parts of the body that radiation (such as X-rays) passes. To put it another way, the thickness of a lesion at spatial positions across the lesion can be determined and the shape and thickness of the body part in which the lesion is situated can be determined from the tomosynthesis data. This means that the spectral information, which can be used to determine for example a number related to the effective atomic number of the material, can also be used to differentiate between materials having equal effective atomic numbers, but which have different densities. The spatial information from the tomosynthesis data is being used with the spectral information in order to improve the characterization of the feature (such as a lesion). In an example, the tomosynthesis data is used with an appropriate image processing algorithm running on the processing unit to determine the delineated boundary. In this manner, the distance rays of radiation pass through the feature can be determined.

In an example, the delineated boundary of the feature is used to determine the extent of radiation interaction in spatial areas. In other words, a 3D sub-volume can be defined (that is governed by the delineated boundary and the angular direction of the plurality of rays of radiation) such that the 3D sub-volume includes the volume of the delineated boundary and "shadow" volumes before and after the delineated boundary such that all volume pixels (voxels) outside of this sub-volume are hit by at least one ray of radiation (e.g., hit by at least one X-ray) in the projection data thereby providing spectral information, where that ray of radiation does not intersect with the feature (e.g. lesion). Then, the (lesion-free) material composition outside the feature, even in the "shadow" volumes, can be determined from the rays of radiation that have not interacted with the feature.

In an example, the processing unit is configured to determine a skin thickness from the plurality of images, and wherein the processing unit is configured to determine at least one material composition of the body part inside the delineated boundary comprising a function of the spectral data inside the delineated boundary and dependent on the at least one material composition inside the at least one portion that is outside the delineated boundary and dependent on the skin thickness.

In an example, material compositions in parts of the body outside of a feature can be accurately determined on the basis of unambiguous spectral radiation data. In some examples, material compositions in some parts of the body outside of the feature are not unambiguous, in that radiation has passed through the feature (see FIGS. 7 and 8). However, unambiguous data outside the feature can be used to augment (and in some cases replace) the ambiguous data outside the feature. In this manner, the material composition around the feature can be determined, and then the spectral data relating to the body part within the delineated boundary of the feature can be used to determine the material compositions within the delineated boundary, where use is made of the knowledge of the material composition around the feature. In some examples, this determination makes use of the spatial extent of the delineated boundary. The spatial extent of the delineated boundary is estimated on the true spatial extent of the feature and can be derived from the spatial information provided by the tomosynthesis data. In other words, knowledge of the spatial extent of the delineated boundary provides volume and length information and provides the ability to discriminate between materials on the basis of their density, not only on the basis of their effective atomic number, which is the case for 2D spectral imaging.

By having a feature that is delineated, in other words having knowledge of the spatial extent or size of the feature (such as a volume), the depth (spatial) information available in tomosynthesis data can be used with the spectral information to differentiate between features comprised of two different materials that have the same effective atomic number, but have different densities. For example, the apparatus is able to differentiate between Calcium Apatite and Calcium oxalate.

In this manner, the apparatus uses depth information available in tomosynthesis data along with spectral information to differentiate between lesion types, for example differentiating between benign and malignant lesions. Furthermore, discrimination between malignant and benign micro-calcifications can be conducted. To put it another way discrimination between (likely benign) cystic from (potentially malignant) solid lesions is provided as well as the discrimination between benign and malignant lesions having the same or overlapping effective atomic numbers, but having different densities.

Figure 7:
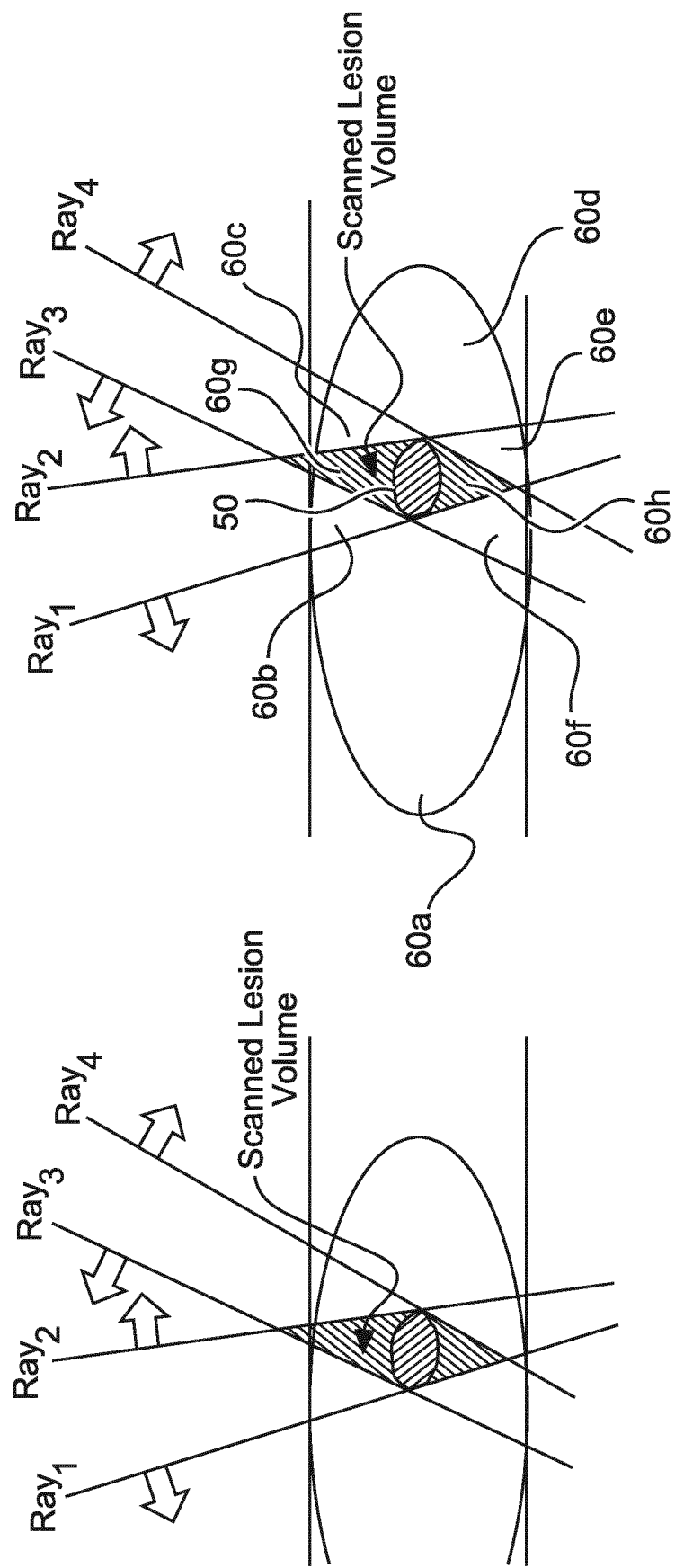
FIG. 7 shows an illustration of a scanned lesion volume for 3D tomosynthesis according to an example of the apparatus shown in FIG. 1 and compared to 2D mammography.
Figure 8:
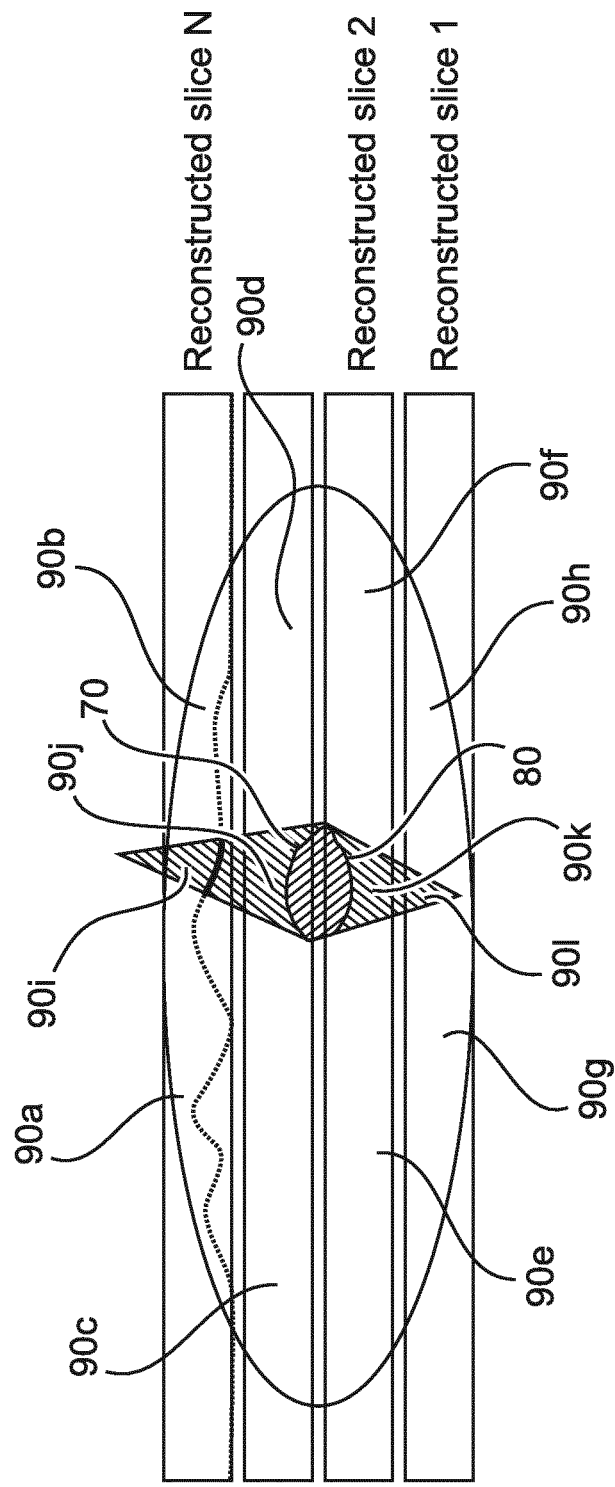
FIG. 8 shows an illustration of interpolation (oscillating curve inside the triangular region) of a breast parameter (oscillating curve outside of the triangular region), according to an example of the apparatus shown in FIG. 1.

According to an example, the at least one portion that is outside the delineated boundary comprises at least one first region 60$g$, 60$h$, 90$i$-90$l$ and at least one second region 60$a$-60$f$, 90$a$-90$h$, see FIGS. 7 and 8. The at least one first region is defined such that every ray of the plurality of rays that passes through the at least one first region also passes through the feature as defined by the delineated boundary 50, 70, 80 and wherein every ray of the plurality of rays that have not passed through the feature as defined by the delineated boundary also have not passed through the at least one first region. The processing unit is then configured to determine at least one material composition of the body part inside the at least one second region as a function of the spectral data in the at least one second region. The processing unit is also configured to determine the at least one material composition of the body part inside the at least one first region as a function of the at least one material composition in the at least one second region.

In other words, tomosynthesis data are acquired over a limited angular range which leads to "shadowing" of a feature (see FIGS. 7 and 8). This means that a feature, such as a lesion, will have an image space both in front of it (towards the radiation source—e.g., an X-ray source) and behind it (away from the radiation source), where all the rays of radiation that pass through these two regions also pass through the feature. These two "shadow" image spaces are the at least one first region. Furthermore, outside of the shadowed regions there will always be at least one ray of radiation (e.g. X-ray) which has not passed through the feature from which spectral data can be obtained. The at least one second region is within this non-shadowed image space. In this manner it is possible to determine the material composition outside of the feature (e.g. lesion) and outside of the shadowed regions. This information can then be used to determine the material composition in the shadowed region.

In an example, data at one depth (within one slice) can be used to determine the material composition in the shadowed region in that slice. However, this need not be the case and the material composition in the shadowed region at one depth (or slice) can make use of data at other depths (other slices).

In an example, the processing unit is configured to determine the at least one region and/or the at least one second region. In an example, the processing unit is configured to determine the at least one region and/or the at least one second region as a function of the delineated boundary of the feature. In an example, the processing unit is configured to determine the at least one region and/or the at least one second region as a function of the delineated boundary of the feature and as a function of angular propagation information for the plurality of rays. In this manner the processing unit can determine those rays of radiation that have passed through the feature and determine those rays of radiation that have not passed through the feature, and can determine the shadow regions on either side of the feature.

In other words, the material composition outside of the shadowed region can be used to determine the material composition within the shadowed region. To put it another way, the material composition within the shadowed region that would have been determined on the basis of the spectral information within the shadowed region can be replaced with data determined on the basis of the material composition outside the shadowed region.

In an example, the at least one portion outside the delineated boundary is in a specific image of the plurality of images and wherein the processing unit is configured to determine the at least one material composition of the body part inside the at least one first region $90i$-$90l$ as a function of the at least one material composition in the at least one second region $90a$-$90h$ for the specific image.

In other words, the determination of the material composition in a part of the shadowed regions can be achieved on the basis of a single tomosynthesis slice. To put this another way each image that has a shadowed region (at least one first region), i.e., where rays that pass through that region also pass through the feature and no rays pass through that region that have not passed through the feature, can make use of the material composition in the non-shadowed region (at least one second region), where there exists at least one ray that does not intersect with the feature, to determine the material composition of the shadowed region (at least one first region). The next slice can be similarly used to determine the material composition in the shadowed region of that slice, and so forth.

In an example, the processing unit being configured to determine the at least one material composition of the body part inside the at least one first region $60g$, $60h$, $90i$-$90l$ comprises interpolation of the at least one material composition in the at least one second region $60a$-$60f$, $90a$-$90h$ into the at least one first region.

In an example, the processing unit being configured to determine the at least one material composition of the body part inside the at least one first region comprises extrapolation of the at least one material composition in the at least one second region. In other words, the shadowed region may be only bounded on one side by a non-shadowed region, but material composition in the non-shadowed region can be extrapolated into the shadowed region to provide values for the material composition in the shadowed region. In an example, the material composition as a function of spatial position in the at least one second region is fitted to a curve equation and determination of the at least one material composition inside the at least one first region comprises this curve equation being interpolated into the at least one first region.

In an example, the material composition as a function of spatial position in the at least one second region is fitted to a curve equation and determination of the at least one material composition inside the at least one first region comprises this curve equation being extrapolated into the at least one first region.

In an example, the material composition as a function of spatial position in the at least one second region is fitted to a surface equation and determination of the at least one material composition inside the at least one first region comprises this surface equation being interpolated into the at least one first region.

In an example, the material composition as a function of spatial position in the at least one second region is fitted to a surface equation and determination of the at least one material composition inside the at least one first region comprises this surface equation being extrapolated into the at least one first region.

In other words, knowledge of the material composition outside of the at least one first region in the at least one second region, and not necessarily all the way around the at least one first region, can be used to determine the material composition inside the at least one first region (shadowed region).

In other words, the material composition outside of the shadowed region can be used to determine the interpolated material composition within the shadowed region. To put it another way, the material composition within the shadowed region that would have been determined on the basis of the spectral information within the shadowed region can be replaced with interpolated data determined on the basis of the material composition outside the shadowed region.

According to an example, the processing unit is configured to determine a geometrical distance travelled by at least one ray of the plurality of rays through the body part, and/or the processing unit is configured to determine a geometrical distance travelled by at least one ray of the plurality of rays through the feature.

In an example, the processing unit is configured to process the tomosynthesis medical data to determine a geometrical distance travelled by at least one ray of the plurality of rays through the body part, and/or determine a geometrical distance travelled by at least one ray of the plurality of rays through the feature.

In an example, the processing unit is configured to determine the total geometrical distance travelled by the at least one ray through the feature. In other words, the thickness of the feature at the position the ray passed through the feature can be determined.

In an example, the processing unit is configured to determine the total geometrical distance travelled by the at least one ray through the body part. In other words, the thickness of the body part at the position the ray passed through the body part can be determined.

In other words, the processing unit is configured to utilize the spatial information contained in the tomosynthesis data to determine for example the spatial extent of a body part such as a breast and to determine the distance a ray travelled through a feature such as a lesion and the distances travelled through the body part either side of the feature (lesion).

According to an example, the feature is annotated directly in at least one of the plurality of images and wherein the processing unit is configured to determine the delineated boundary 50, 70, 80 of the feature as a function of the annotated feature.

In an example, a feature contour is annotated in one image of the plurality of images, and the feature contour in other images that contain image data of the feature is determined by back and forward projecting the annotated feature contour through the reconstruction volume.

In an example, a feature contour is annotated in all the images of the plurality of images that contain image data of the feature.

In this manner, the processing unit determines a delineated boundary of the feature.

In other words, a delineated boundary of the feature can be defined that can represent an estimation of the actual shape of the feature. This enables an accurate determination of the rays of radiation that do not pass through the at least one first region to be made. In other words the rays that pass through the at least one second region can be determined. This also enables an accurate determination of the rays of radiation that have passed through the at least one first region. This also enables an accurate determination of the shadowed regions of the body part, where only rays of radiation that have passed through the feature pass through the shadowed region. In an example, this enables an accurate determination of the spatial extent of the at least one first region and an accurate determination of the spatial extent of at least one second region.

According to an example, the medical data comprises a combined image of at least two of the plurality of images and wherein the feature is annotated directly in the combined image, and wherein the processing unit is configured to back propagate the annotated feature in the combined image into at least one of the plurality of images that comprises data of the feature to determine the delineated boundary 50, 70, 80 of the feature. In an example, the processing unit is configured to back propagate the annotated feature in the combined image into at least one of the plurality of images that comprises data of the feature by automatic retrieval of a focal plane to determine the delineated boundary 50, 70, 80 of the feature.

In an example, the processing unit is configured to combine at least two of the plurality of images to generate the combined image.

In other words, a 3D delineated boundary around the feature can be determined.

In an example, the feature is annotated directly by a user.

In an example, the processing unit is configured to determine at least one material composition of the body part inside the delineated boundary within the combined image as a function of the spectral data inside the delineated boundary, and to characterise the feature as a function of the material composition inside the delineated boundary. In other words, characterization is carried out directly in the combined image. This would be a straight-forward fast implementation and the results would be directly comparable to a 2D algorithm.

According to an example, the delineated boundary 50, 70, 80 of the feature comprises a three-dimensional shape model of the feature, and wherein the processing unit being configured to determine the at least one material composition of the body part inside the delineated boundary comprises utilising the three-dimensional shape model of the feature.

In other words, the determined shape of the delineated feature can be used as additional information for determining the material composition inside the at least one portion and inside the delineated boundary.

In an example, the processing unit is configured to determine the three-dimensional shape model of the feature. In an example, the processing unit is configured to determine the three-dimensional shape model of the feature as a function of the feature annotated in the at least one of the plurality of images. In an example, the processing unit is configured to determine the three-dimensional shape model of the feature as a function of the feature annotated in the combined image.

According to an example, the processing unit being configured to determine the at least one material composition of the body part inside the delineated boundary comprises utilising calculated spectral features of at least two materials for the at least two energies of the plurality of rays of radiation.

In an example, determining the at least one material composition of the body part inside the delineated boundary comprises utilizing a look up table. In an example, the look up table is populated with the system response to various combinations of two reference materials (e.g., aluminium and polyethylene). In an example, the spectral features relate to at least one material composition that comprises a breast tissue composition. In an example, the at least one material composition is derived from a spectral feature. In an example, the spectral features relates to a cystic volume fraction. In an example, the spectral features relates to an equivalent cystic lesion diameter. In other words, in an example the material composition can be the division of the breast into some given materials such as adipose and glandular tissue. From this material composition, derived from a spectral material decomposition, various features can be derived. These derived features may comprise a cystic volume fraction, an equivalent cystic diameter, breast density value and the like.

Figure 2:
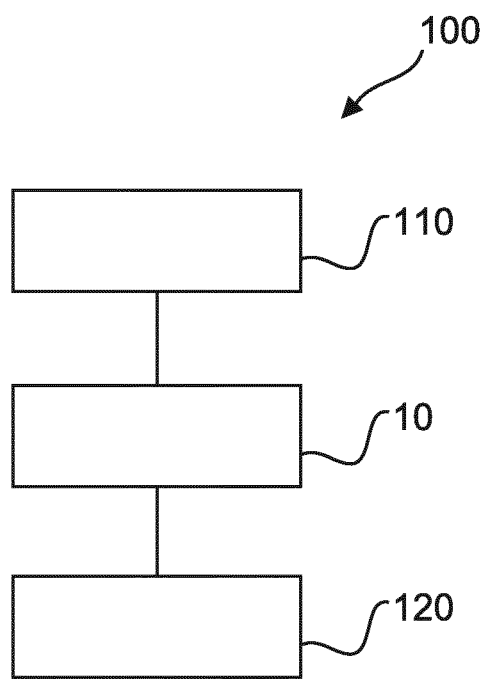
FIG. 2 shows a schematic set up an example of a medical system apparatus for characterization of a feature in a body part.

FIG. 2 shows a medical system 100 for characterization of a feature in a body part. The system 100 comprises an image acquisition unit 110, an apparatus 10 for characterization of a feature in a body part, and a display unit 120. The image acquisition unit 110 is configured to provide the medical data of a body part to the apparatus 10 via communication means (not shown). The display unit 120 is configured to display at least one of the plurality of X-ray images along with data representative of the feature.

In an example, the image acquisition unit comprises an X-ray imaging device, for example, a tomosynthesis arrangement.

Figure 3:
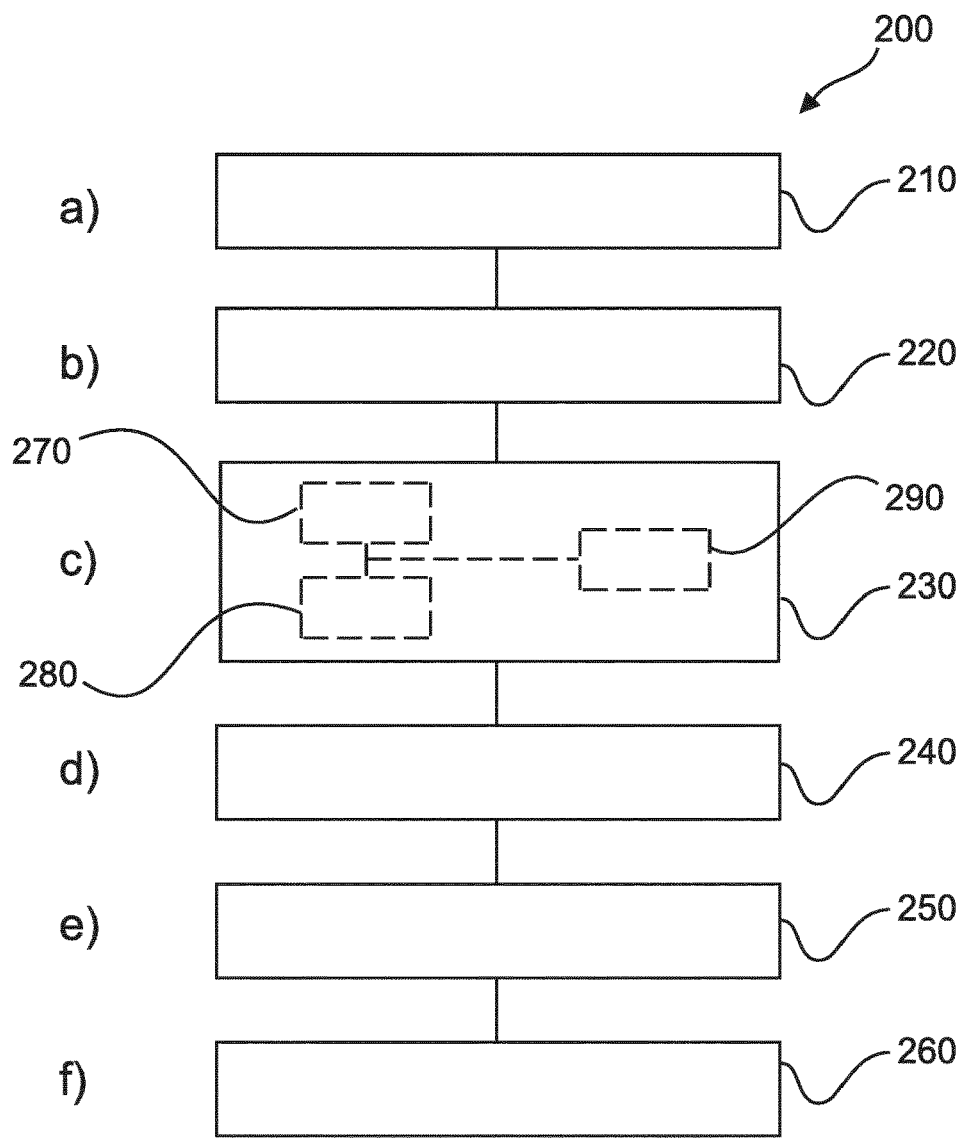
FIG. 3 shows a schematic set up an example of a method for characterization of a feature in a body part, where step c) is optional.

FIG. 3 shows a method 200 for characterization of a feature in a body part in steps, where some steps shown in the figure are however optional. The method comprises the following:

In a providing step 210, also referred to as step a), tomosynthesis medical data comprising a plurality of images of the body part is provided, wherein the plurality of images comprise image data associated with a plurality of rays of radiation that have passed through the body part, wherein the image data comprises spectral data associated with at least two energies of the plurality of rays of radiation, wherein the medical data comprises data of the feature.

In a first determining step 220, also referred to as step b), a delineated boundary of the feature is determined.

In a second determining step 240, also referred to as step d), at least one material composition of the body part inside the delineated boundary is determined comprising a function of the spectral data inside the delineated boundary; In a characterizing step 250, also referred to as step e), the feature is characterised as a function of the at least one material composition inside the delineated boundary of the feature.

In an outputting step 260, also referred to as step f), data representative of the feature is output.

According to an example, the method comprises: in a determining step 230, also referred to as step c), at least one material composition of the body part inside at least one portion of at least one image of the plurality of images is determined as a function of the spectral data inside at least a part of the at least one portion, wherein the at least one portion is outside the delineated boundary; and wherein step d) comprises determining 240 at least one material composition of the body part inside the delineated boundary dependent on the at least one material composition inside the at least one portion that is outside the delineated boundary.

According to an example, the at least one portion that is outside the delineated boundary comprises at least one first region and at least one second region, wherein the at least one first region is defined such that every ray of the plurality of rays that passes through the at least one first region also passes through the feature as defined by the delineated boundary and wherein every ray of the plurality of rays that have not passed through the feature as defined by the delineated boundary also have not passed through the at least one first region, and wherein step c) comprises determining 270 at least one material composition of the body part inside the at least one second region as a function of the spectral data in the at least one second region, and wherein step c) comprises determining 280 the at least one material composition of the body part inside the at least one first region as a function of the at least one material composition in the at least one second region.

In an example, the at least one portion outside the delineated boundary is in a specific image of the plurality of images and wherein step c) comprises determining the at least one material composition of the body part inside the at least one first region as a function of the at least one material composition in the at least one second region for the specific image.

According to an example, step c) comprises interpolating 290 the at least one material composition in the at least one second region into the at least one first region.

In an example, the method comprises determining a geometrical distance travelled by at least one ray of the plurality of rays through the body part, and/or determining a geometrical distance travelled by at least one ray of the plurality of rays through the feature.

In an example, the method comprises annotating the feature directly in at least one of the plurality of images and determining the delineated boundary of the feature as a function of the annotated feature.

In an example, the medical data comprises a combined image of at least two of the plurality of images and wherein the method comprises annotation of the feature directly in the combined image, and wherein determining the delineated boundary of the feature comprises back propagating the annotated feature in the combined image into at least one of the plurality of images that comprises data of the feature.

In an example, the delineated boundary of the feature comprises a 3D shape model of the feature, and wherein determining the at least one material composition of the body part inside the delineated boundary comprises utilising the 3D shape model of the feature.

In an example, determining the at least one material composition of the body part inside the delineated boundary comprises utilising calculated spectral features of at least two materials for the at least two energies of the plurality of ray of radiation.

The following relates to a detailed description of an example of the apparatus and method for the characterization of a feature in a body part. To facilitate an understanding of the features of the apparatus, and the steps of the method in such detailed examples, the physical understanding of model assumptions that can be made to the interaction of radiation in the form of X-rays with matter will be presented. An understanding of how materials can be characterised in images is presented.

Introduction

Spectral X-ray imaging allows differentiation between given tissue types, provided their spectral absorption characteristics differ measurably. For example, spectral imaging can be enabled through the use of an energy-resolving photon-counting detector. Two (or more) energy thresholds of the detector allow differentiation between high-energy and low-energy X-ray photons. In this way, a tomosynthesis spectral mammogram, i.e. a paired set of images at different depths through the breast from the high- and low-energy channels can be acquired with one single exposure and at no additional dose to the patient. This enables the characterization of breast lesions. Such lesions identified in mammographic screening will help to reduce the number of recalls for cysts. Solitary well defined mass lesions are a common mammographic finding, contributing approximately 20% of overall recalls at screening. A large number of these lesions when assessed with ultrasound are simple cysts which do not require further clinical evaluation. Furthermore, studies have demonstrated that cancer rates in solid probably benign lesions are less than 2%. Improving lesion characterization at screening would be desirable to reduce both the costs of the screening program as well as patient anxiety. The present apparatus, system, and method described meet this aim.

Discrimination of cyst fluid from solid tissue using spectral X-ray data has been demonstrated to be feasible in specimen experiments, which characterised the energy-resolved X-ray attenuation of cyst fluid and solid formalin fixed lesions. The present apparatus, system and method, through making use of calibration routines and a spectral discrimination algorithm translate these specimen results into clinical practice. Based on the energy-dependent X-ray attenuation of cyst fluid, carcinoma, adipose and glandular tissue, a breast lesion model, which estimates both the local breast tissue composition and the lesion composition, is generated per mammographic view in order to discriminate solid from cystic lesions. From the estimated lesion composition, an algorithm can be developed to predict the total cystic volume and the fraction of cystic volume in the lesion from the spectral measurements in the lesion and in a lesion-free reference region. Both features can be combined in a linear discriminator for the task of discriminating cystic from solid lesions.

Spectral Imaging

Note, a detailed description of spectral imaging, including the discussion below, can be found in the following paper: Fredenberg E, Kilburn-Toppin F, Dance D R, Willsher P, Moa E, Young K C, Wallis Fredenberg E, Kilburn-Toppin F, Dance D R, Willsher P, Moa E, Young K C, Wallis M G, "Measurement of breast-tissue x-ray attenuation by spectral mammography: solid lesions", Phys Med Biol (submitted for publication, 2015).

For most natural body constituents at mammographic X-ray energies (approximately 15-40 keV), it is fair to ignore absorption edges. X-ray attenuation is then made up of only two interaction effects, namely photoelectric absorption and scattering processes. Accordingly, in the mammographic energy range, a linear combination of any two materials of different and low atomic number can approximately simulate the energy-dependent attenuation of a third material, for instance breast tissue, of a given thickness, $$t_{breast}\mu_{breast}(E) = t_1\mu_1(E) + t_2\mu_2(E). \quad (1)$$

These materials can be called reference materials, and if this relationship is assumed to hold exactly, then the associated normalized reference thicknesses $[t_1, t_2]/t_{breast}$ are unique descriptors of the energy dependent sample attenuation ($\mu_{breast}$) given the known attenuations of the reference materials ($\mu_1$ and $\mu_2$). Further, and with the same assumption, the detected signal (1) in a photon-counting X-ray detector would be identical for a tissue sample and for the equivalent combination of reference materials, regardless of incident energy spectrum ($\Phi(E)$) or detector response ($\Gamma(E)$), $$I_{breast} = I_0 \int \exp[-t_{breast}\mu_{breast}(E)]\Phi(E)\Gamma(E)dE \quad (2)$$
$$= I_0 \int \exp[-t_1\mu_1(E) - t_2\mu_2(E)]\Phi(E)\Gamma(E)dE$$
$$= I_{reference}.$$

Hence, measurements of attenuation at two different energies (or for two different energy spectra) yield a non-linear system of equations, which, for known $t_{breast}$, can be solved for $t_1$ and $t_2$. Measurements at more than two energies yield an over-determined system of equations under the assumption of only two independent interaction processes, and would, in principle, be redundant. Equations 0 and 0 assume that scattering processes can be treated as absorption, which is true only for X-ray detector geometries with efficient scatter rejection, such as multi-slit.

The equivalent thicknesses of reference materials can be expressed in terms of a vector with magnitude and angle given by $$r = \sqrt{t_1^2 + t_2^2} \text{ and } \theta = \tan^{-1}\left(\frac{t_1}{t_2}\right). \quad (3)$$

The magnitude r is directly proportional to the thickness and the density (specific weight) of the sample, whereas the angle θ is related to the attenuation energy dependence and the (effective) atomic number of the material, and is independent of sample thickness.

A practical example of reference materials are aluminium (Al) and polymethyl methacrylate (PMMA). Following the discussion above, a spectral calibration look-up table can be generated by measuring the photon counts in both energy bins for a series of Al and PE combinations. The look-up table can be used to convert the photon counts of any spectral measurement by material decomposition into Al and PE components. The energy-dependent linear attenuation coefficients are known for adipose and glandular tissue as well as for breast tumours and fibro-adenomas. More recently these constants have been measured for cyst fluid and tumour tissue on a spectral MicroDose prototype system, demonstrating the discriminability of cysts from tumours in an in-vitro experiment—for example, see Fredenberg E, Dance D R, Willsher P, et al. Measurement of breast-tissue x-ray attenuation by spectral mammography: First results on cyst fluid. Phys Med Biol. 2013; 58:8609-8620.

Knowing these coefficients it is possible to solve for the composition of any mixture of two known constituents from the high-energy and low-energy measurements from a spectral tomosynthesis mammogram. Spectral volumetric breast density measurement, for example, assumes that the breast can be modelled as a combination of only adipose and glandular tissue, and uses this material decomposition to compute the fraction of glandular tissue volume to the overall breast volume as breast density value. If there are more than two tissue compartments, the information from the two energy bins is insufficient to uniquely determine the tissue composition inside the breast. Hence, additional model assumptions have to be introduced. Refining the breast model by including an additional layer of skin, for example, requires an estimate of the thickness of the skin layer and knowledge of the energy-dependent linear attenuation coefficient of skin tissue in order to solve for the unknown breast density from the spectral measurements.

Lesion Characterization—a 2D Illustrative Example

Figure 4:
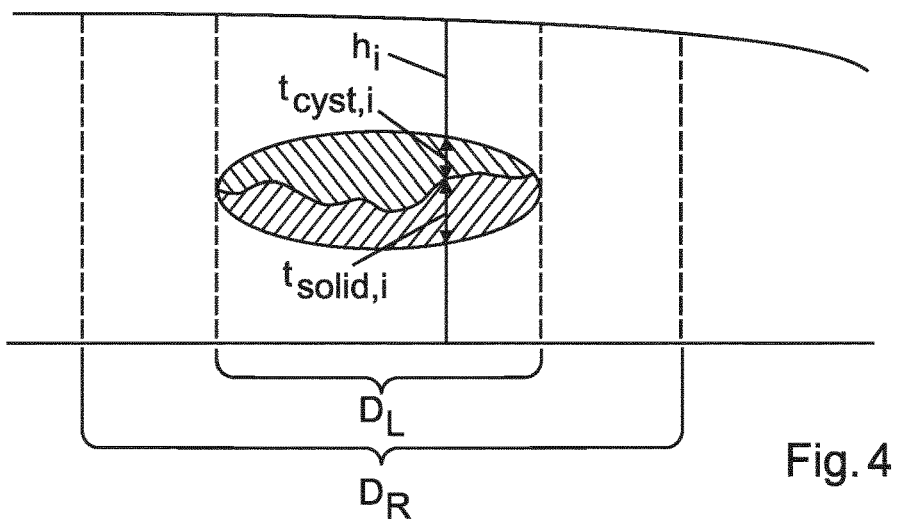
FIG. 4 shows a schematic illustration of a lesion with cystic and solid constituents within surrounding breast tissue.

FIG. 4 shows an illustration of a lesion with cystic and solid constituents within surrounding breast tissue. Lesion characterization from spectral mammography aims at characterizing the composition of a cystic or solid lesion within a surrounding mixture of adipose and glandular tissue. The underlying model assumes that the spectral measurement in each pixel i can be described by a certain thickness $t_{cyst,i}$ of cyst fluid, a certain thickness $t_{solid,i}$ of solid tissue, which add together with the remaining thickness of the surrounding mixture of adipose and glandular tissue to the total breast thickness $h_i$. From the estimated model parameters $t_{cyst,i}$ and $t_{solid,i}$, a discriminator is derived indicating the likelihood of the lesion being either cystic or solid.

To solve for the unknown lesion composition parameters $t_{cyst,i}$ and $t_{solid,i}$, estimates on the local breast composition and the breast thickness $h_i$ are required in the lesion region $D_L$. The local breast composition estimate is derived from a local lesion-free neighborhood $D_R$ by interpolation, and for tomosynthesis data the height information can be estimated from the inherent depth information available or derived by interpolation. Both regions $D_L$ and $D_R$ and the extent of the lesion can defined by user annotation in the tomosynthesis data or in a 2D spectral mammogram derived from that tomosynthesis data. The regions can also be annotated through the use of image processing.

The lesion parameters $t_{cyst,i}$ and $t_{solid,i}$ can be computed by solving a linear system of equations to estimate the overall cystic ($V_{cyst}$) and solid ($V_{solid}$) volume components.

For discriminating cystic from solid lesions, the relative cystic volume fraction is used as one discriminating feature $$CVF = \frac{V_{cyst}}{V_{lesion}}, \text{ with } V_{lesion} = V_{cyst} + V_{solid}, \quad (4)$$

A second discriminator feature is derived from the absolute cystic volume $V_{cyst}$, which is expected to grow with the lesion diameter as a cubic function. To correct for this non-linearity, an equivalent cystic diameter (ECD) and an equivalent lesion diameter (ELD) are computed via $$ECD = \sqrt[3]{\frac{6V_{cyst}}{\pi}} \text{ and } ELD = \sqrt[3]{\frac{6V_{lesion}}{\pi}} \quad (5)$$

as the diameter of a spherical lesion with the same volume as $V_{cyst}$ and $V_{lesion}$, respectively. Both features are then combined in a two-dimensional linear discriminator for the task of discriminating cystic from solid lesions from spectral mammography. This method of characterization has been described for the 2D case for ease of description, but can be applied to the 3D case with respect to tomosynthesis data.

Spectral Tomosynthesis

Although the discrimination of cystic from solid lesions by spectral X-rays has been shown to be feasible, the discrimination is far from perfect with a specificity of about 50% at the 99% sensitivity level. This means that 50% of cysts would be erroneously characterised as tumours, which would lead to unnecessary recalls. More serious is, however, the fact that 1% of the solid lesions, and hence potentially malignant tumours, might be erroneously characterised as cysts and potentially misdiagnosed. There is, in other words, a need to improve lesion characterization. The present apparatus, system and method effect this improvement.

With the present apparatus, system and method it is possible to improve this breast composition estimate because spatial information in the depth direction from tomosynthesis data can be utilised and the scanned lesion volume can be accurately determined, see FIGS. 7 and 8 discussed below. Moreover, 3D tomosynthesis also enables an estimate on the lesion height, which can be used for example as an upper bound on the computed lesion thickness in the lesion characterization algorithm. The geometrical shape and size of the lesion and of the surrounding breast can be determined. The "shadow" volume areas (at least one first region) either side of the lesion can also be determined, where the X-rays that have passed through these regions also have passed through the lesion and the volume areas outside of the "shadow" volume areas (at least one second region) can be determined, where at least one X-ray passes through this region that has not gone through the lesion.

A particular issue relates to the physical nature of the problem being faced, i.e. in the fact that X-ray attenuation in soft tissue is to a good approximation made up of only two independent interaction effects: Compton scattering; and the photoelectric effect. It is therefore intrinsically not possible to distinguish between more than two features in a (spectral) X-ray projection of the breast, but discrimination between five features is required: the amounts of adipose tissue, glandular tissue, skin, cyst fluid (would be close to zero for a solid lesion), and tumor tissue (would be close to zero for a cyst).

Figure 5:
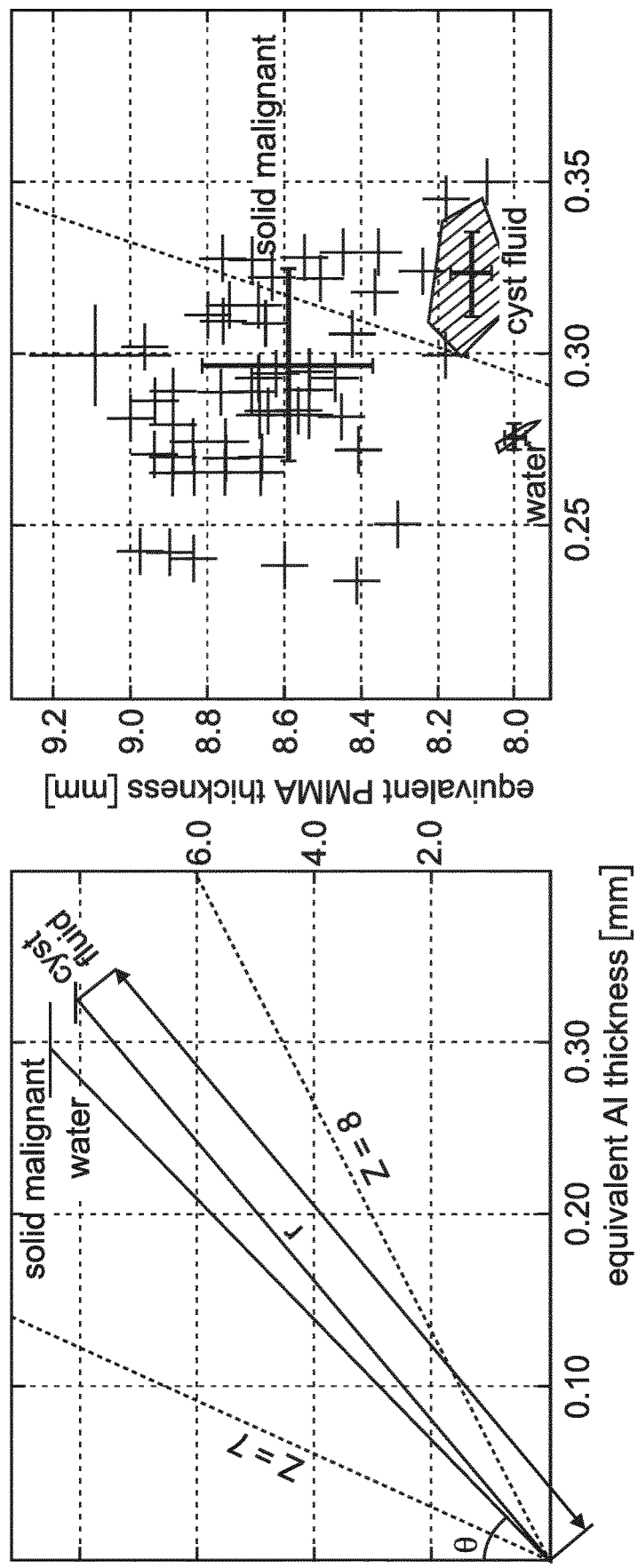
FIG. 5 shows equivalent PMMA and Al thickness (normalized to a 10 mm sample) for malignant solid lesions, cyst fluid and water. This figure is derived from the following paper: Fredenberg E, Kilburn-Toppin F, Dance D R, Willsher P, Moa E, Young K C, Wallis Fredenberg E, Kilburn-Toppin F, Dance D R, Willsher P, Moa E, Young K C, Wallis M G, "Measurement of breast-tissue x-ray attenuation by spectral mammography: solid lesions", Phys Med Biol (submitted for publication, 2015).

FIG. 5 shows equivalent PMMA and Al thickness (normalized to a 10 mm sample) for solid lesions (benign and malignant), cyst fluid and water. Left: Overview of the Al-PMMA vectors with the angle θ and magnitude r indicated on the water vector. Dotted lines indicate θ for atomic numbers Z=7 and Z=8. Right: Close-up of the measurement points. Each individual measurement is shown for the solid lesions. For cyst fluid and water, the perimeters (convex hulls) of the set of individual measurement points are shown.

The data in FIG. 5 therefore identifies a challenge faced in characterizing features, where attenuation measurements of aspirated cyst fluid and excised tumour tissue are shown. This challenge is addressed by the present apparatus, system and method. As the attenuation of typical breast tissue is modelled to be made up of only two interaction effects, it can be uniquely described by the combination of any other two materials (in this case aluminium—Al—and Plexiglas—PMMA). These equivalent material thicknesses may in turn be described by the angle (θ) and magnitude (r) of the Al-PMMA vector, ranging from the origin to the Al-PMMA point of the material. The angle depends on the atomic number of the material, whereas the magnitude is proportional to the density (specific weight) and to the thickness of the material. Spectral imaging enables a measurement of both r and θ, but it is only θ that is useful for discrimination between materials as long as the thickness is unknown; it is not possible to differentiate between a thin and dense target, and a thicker but less dense target if θ is equal for both targets. The dotted line in FIG. 5 indicates the outermost sample, in terms of θ, of the cyst-fluid distribution. Even though no solid samples fall within the shaded region of the cyst distribution (i.e. no overlap in terms of θ and r), 29% of the malignant samples overlap with the cyst distribution in terms of θ (FIG. 5, area below the dotted line), and are therefore not possible to distinguish from cyst fluid from a 2D spectral mammogram. This sets an upper limit for the performance of the current version of the lesion characterization tool.

Figure 6:
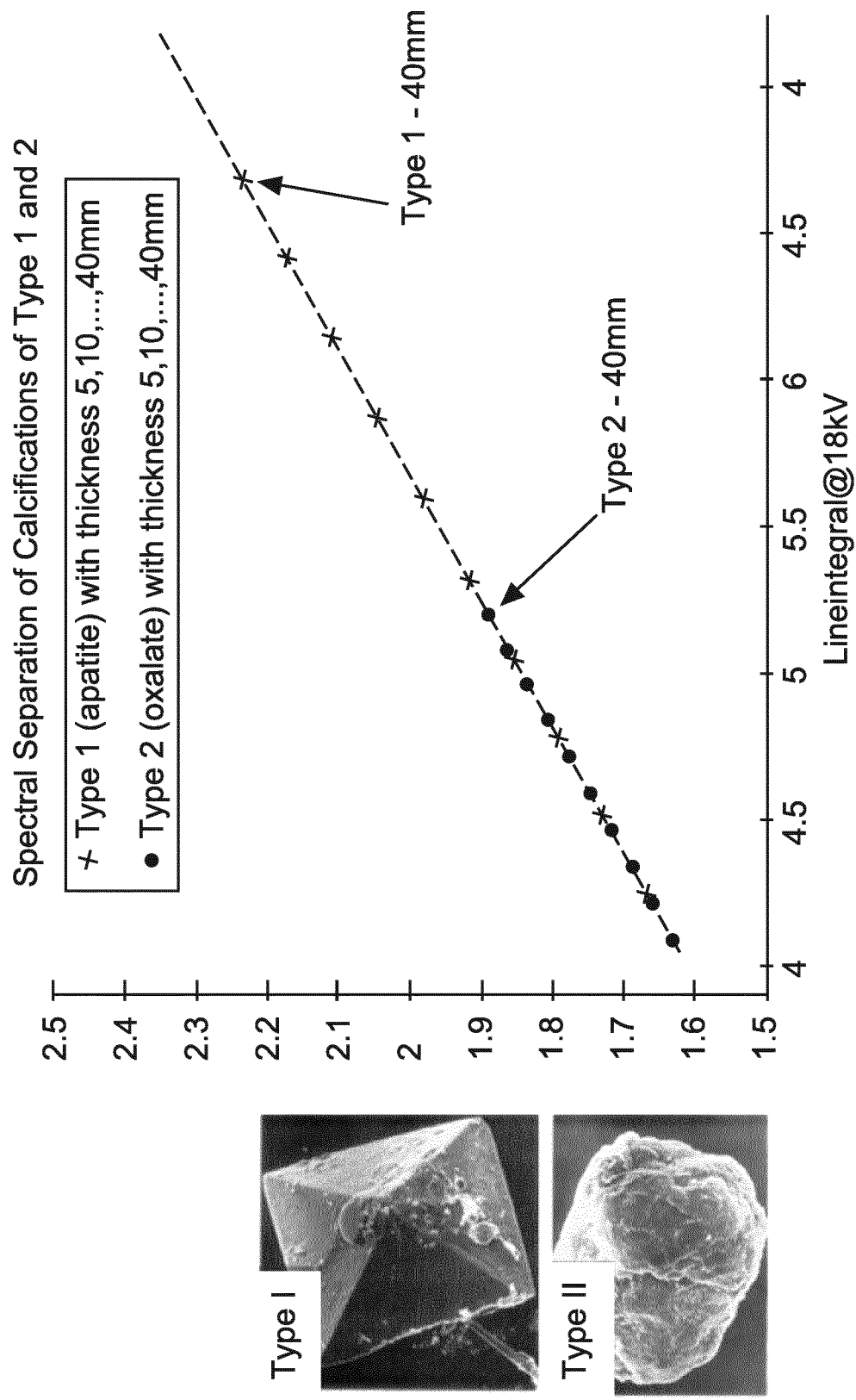
FIG. 6 shows images of type I (likely benign) and type II (likely malignant) calcifications, with the plot showing the attenuation of the two types of calcification imaged at two different energy spectra.

FIG. 6 identifies another issue that the present apparatus, system and method address. FIG. 6 shows images of calcifications: Type I (likely benign) consisting of calcium oxalate (CaC2O4) and type II (likely malignant) consisting of Calcium Apatite (Ca5(PO4)3(OH)), (Wang, Z et al., "Non-invasive classification of microcalcifications with phase-contrast X-ray mammography." Nature communications 5 (2014)), with the plot showing the attenuation of the two types of calcification at two different energy spectra. In other words, FIG. 6 shows the attenuation of two types of calcifications at two different energy spectra. There is overlap in terms of θ but not in terms of r. Type I and Type II calcifications have different densities, which leads to different r values, but the effective atomic numbers, and therefore θ, are essentially the same and it is not possible to distinguish between the two types using conventional implementations of spectral imaging.

However, the present apparatus, system and method address this issue, where lesion characterization on spectral tomosynthesis data (synthetic 2D views or directly in the 3D volume) is provided. This is achieved by taking advantage of the additional spatial information offered by the tomosynthesis reconstruction to mitigate uncertainties introduced by approximations and assumptions, and to enable characterization of lesion types with overlapping θ.

Detailed Description of the Present Apparatus, System and Method

The height information available in tomosynthesis is used together with spectral information to differentiate between lesion types, typically between benign and malignant lesions. The height information enables characterization, not only in terms θ, but also in terms of r. In general, the characterization will include the following steps:

Lesion annotation by the radiologist in the tomosynthesis volume or in the synthetic mammogram to automatically derive an estimated lesion region in the tomosynthesis volume reconstruction.

The spectral tomosynthesis data are used to measure the breast tissue composition outside (in three dimensions) the lesion region.

Interpolation of the measured breast tissue composition to parts of the volume that are outside the lesion region (in 3D) but that are not possible to image without shadowing by the lesion because of the limited angular range of tomosynthesis (the "scanned lesion volume" in FIGS. 7 and 8).

Calculating spectral features such as the cystic volume fraction and the equivalent cystic lesion diameter from data within the lesion region by removing the influence of breast tissue outside the lesion region.

Using the calculated spectral features to estimate the lesion type from a pre-defined selection. The discrimination is typically done between benign and malignant lesions.

In More Detail

In an example, the additional depth information of the tomosynthesis reconstruction is used as follows:
1. The lesion contour is annotated by a radiologist either directly in the focal slice of the 3D tomosynthesis reconstruction (i.e. the slice where the centre of the lesion is located) or the lesion contour is annotated in a 2D visualization of the 3D volume (for instance a sum of all slices) and then back-propagated into the reconstruction volume by automatic retrieval of one or several slices where the lesion is in focus. For instance, this may be achieved by determining one or several slices corresponding to the maximum or highest intensities within the lesion region, or by determining one or several slices corresponding to the maximum or highest entropies within the lesion region.
2. The scanned lesion region is computed by propagation of the lesion contour from the focal slice through the reconstruction volume (FIG. 7). In this way, a 3D sub-volume can be defined, such that all voxels outside this sub-volume are hit by at least one X-ray in the projection data, which does not intersect with the lesion. Therefore, it is possible to estimate a lesion-free breast composition outside the scanned lesion region from those X-rays, which do not intersect with the lesion in a second step.
3. The breast composition inside the scanned lesion region (FIGS. 7 and 8) can be estimated by interpolating the values of the lesion-free breast composition outside the scanned lesion region. This interpolation is performed in each slice reconstruction (FIG. 8).
4. A lesion-free 2D visualization is computed from the original reconstruction by replacing the values inside the scanned-lesion region with the estimated ones from the interpolated lesion-free composition per slice and then combining all slices. The lesion is then characterised as described above, where data from around the lesion including lesion free regions above and below have been used.

In an example, the additional depth information of the tomosynthesis reconstruction is used to improve the lesion characterization as follows:

The user annotated lesion contour in the 2D visualization of the 3D volume is back-propagated into each slice of the stack of tomosynthesis slice reconstructions.

Based on the edge-conspicuity of the back-propagated contour in each slice reconstruction, a 3D shape model is fitted to the back-propagated lesion contour.

The estimated 3D shape model of the lesion can be used as an additional prior in the lesion characterization algorithm, for example as an upper bound on the maximum allowed lesion thickness as derived by the lesion characterization algorithm.

In this example, the discrimination of Type I from Type II calcifications can be effected by exploiting the estimated thickness estimate. The discrimination can then be derived from the difference in attenuation of Type I and Type II calcifications, which would not be possible without any thickness information due to the similar spectral angle θ of the two calcification types.

In an example, the user annotation is performed in a reconstructed slice instead of a in a 2D visualization. In this case, the annotated lesion contour is forward propagated through the volume onto the 2D visualization and the algorithm may be applied as described in the previous embodiments.

In an example, the depth information offered by tomosynthesis is further employed to estimate the skin thickness for improved modelling, or to exclude the skin altogether from the measurement. This example can applied in combination with any of the previous examples.

In an example the above described method of characterizing a lesion is applied directly on a 2D visualization of the 3D volume (e.g. a sum of all slices) without using the additional spatial information of the tomosynthesis system. In this way, a straight forward fast implementation is provided.

FIG. 7 shows a scanned lesion volume of a tomosynthesis scan, which is defined by the X-ray beams Ray1, Ray2, Ray3, Ray4. These X-rays are defined by the system geometry and define the border of the part of the projection data, which does not intersect with the lesion under investigation. The feature (lesion) has a delineated boundary 50. Two regions 60g and 60h outside of the delineated boundary 50 of the feature are characterised in that all the X-rays that pass through these regions also pass through the feature. Regions 60a-60f that are also outside of the delineated boundary are characterised in that at least one X-ray passes through them that has not passed through the feature. Therefore, spectral information in regions 60a-60f can be used to determine the material composition in those regions and then used to determine the material composition in regions 60g and 60h.

FIG. 8 shows an illustration of an interpolation (curve in the truncated triangular region scanned lesion region) of a breast parameter (curve outside of the truncated triangular region). FIG. 8 shows the individual slices of tomography image data that make up a volume scan, as shown in FIG. 7. The feature (lesion) has delineated boundaries 70 and 80 in two of the image slices. Again, there are volume regions 90i, 90j, 90k, and 90l that are characterised in that all the X-rays that pass through these regions also pass through the feature (shadow regions). Again regions 90a-90h that are outside of the delineated boundary are characterised in that at least one X-ray passes through them that has not passed through the feature. A breast parameter (for example the local amount of dense tissue) can be estimated outside the scanned lesion region without being affected by the cystic or solid lesion content. Inside the shadow region, this measurement would be impaired because each X-ray passes through potentially four different tissue types (adipose, glandular, cystic and/or solid tissue) and hence cannot be exactly represented by a two-compartment model. However, by interpolating the value outside the shadow region into the shadow region, an estimate can be made of the value in the shadow region.

In another exemplary embodiment, a computer program or computer program element is provided that is characterised by being configured to execute the method steps of the method according to one of the preceding embodiments, on an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for characterizing a lesion in a breast, comprising:
    a memory containing instructions; and
    processing circuitry for executing the instructions to configure the apparatus to:
        process tomosynthesis medical data comprising a plurality of images of the breast, wherein the plurality of images comprise image data associated with a plurality of X-rays that have passed through the breast, wherein the image data comprises spectral data associated with at least two photon energy levels of the plurality of X-rays, wherein the medical data comprises data of the lesion;
        determine a delineated boundary of the lesion;
        determine at least one material composition of the breast inside at least one portion of at least one image of the plurality of images as a function of the spectral data inside at least a part of the at least one portion, wherein the at least one portion is outside the delineated boundary;
        determine at least one material composition of the breast inside the delineated boundary dependent on the at least one material composition inside the at least one portion that is outside the delineated boundary;
        characterize the lesion as a function of the at least one material composition inside the delineated boundary; and
        output data representative of the lesion.

2. The apparatus according to claim 1, wherein the processing circuitry is configured to determine a geometrical distance travelled by at least one X-ray of the plurality of X-rays through at least one of the breast and lesion.

3. The apparatus according to claim 1, wherein the lesion is annotated directly in at least one of the plurality of images, and wherein the processing circuitry is configured to determine the delineated boundary of the lesion as a function of the annotated feature.

4. The apparatus according to claim 1, wherein the medical data comprises a combined image of at least two of the plurality of images, and wherein the lesion is annotated directly in the combined image, and wherein the processing circuitry is configured to back propagate the annotated lesion in the combined image into at least one of the plurality of images that comprises data of the lesion to determine the delineated boundary of the lesion.

5. The apparatus according to claim 1, wherein the delineated boundary of the lesion comprises a three-dimensional shape model of the lesion, and wherein the processing circuitry being configured to determine the at least one material composition of the breast inside the delineated boundary comprises utilizing the three dimensional shape model of the lesion.

6. The apparatus according to claim 1, wherein the processing circuitry being configured to determine the at least one material composition of the breast inside the delineated boundary comprises utilizing calculated spectral features of at least two materials for the at least two energies of the plurality of X-rays.

7. A medical system for characterizing a lesion in a breast, the system comprising:
the apparatus according to claim 1; and
a display for displaying the data representative of the lesion.

8. A method for characterizing a lesion in a breast, comprising:
providing tomosynthesis medical data comprising a plurality of images of the breast, wherein the plurality of images comprise image data associated with a plurality of X-rays that have passed through the breast, wherein the image data comprises spectral data associated with at least two photon energy levels of the plurality of X-rays, wherein the medical data comprises data of the lesion;
determining a delineated boundary of the lesion;
determining at least one material composition of the breast inside at least one portion of at least one image of the plurality of images as a function of the spectral data inside at least a part of the at least one portion, wherein the at least one portion is outside the delineated boundary;
determining at least one material composition of the breast inside the delineated boundary dependent on the at least one material composition inside the at least one portion that is outside the delineated boundary;
characterizing the lesion as a function of the at least one material composition inside the delineated boundary; and
outputting data representative of the lesion.

9. A non-transitory computer readable medium storing instructions, which, when executed on processing circuitry, cause the processing circuitry to perform the method according to claim 8.

* * * * *